(12) United States Patent
Cheung et al.

(10) Patent No.: US 7,309,798 B2
(45) Date of Patent: Dec. 18, 2007

(54) PROCESS FOR CARBONYLATION OF ALKYL ETHERS

(75) Inventors: Patricia Cheung, Berkeley, CA (US); Enrique Iglesia, Moraga, CA (US); John Glenn Sunley, East Yorkshire (GB); Aditya Bhan, Berkeley, CA (US); David John Law, East Yorkshire (GB)

(73) Assignees: The Regents of the University of California, Oakland, CA (US); BP Chemicals Limited, Middlesex (GB)

( * ) Notice: Subject to any disclaimer, the term of this patent is extended or adjusted under 35 U.S.C. 154(b) by 0 days.

(21) Appl. No.: 11/417,415

(22) Filed: May 3, 2006

(65) Prior Publication Data

US 2006/0287551 A1 Dec. 21, 2006

Related U.S. Application Data

(63) Continuation-in-part of application No. 11/123,581, filed on May 5, 2005, now abandoned.

(51) Int. Cl.
*C07C 67/36* (2006.01)
(52) U.S. Cl. .................................... 560/232
(58) Field of Classification Search ............ None
See application file for complete search history.

(56) References Cited

U.S. PATENT DOCUMENTS

| | | | |
|---|---|---|---|
| 3,130,007 A | 4/1964 | Breck | |
| 3,689,533 A | 9/1972 | Schultz | |
| 4,076,842 A | 2/1978 | Plank et al. | |
| 4,612,387 A | 9/1986 | Feitler | |
| 5,189,203 A | 2/1993 | Hansen et al. | |
| 5,218,140 A | 6/1993 | Wegman | |
| 5,238,675 A | 8/1993 | Rawlence et al. | |
| 5,286,900 A | 2/1994 | Hansen et al. | |
| 5,420,345 A | 5/1995 | Smith | |
| 5,728,871 A | 3/1998 | Joensen et al. | |
| 5,763,654 A | 6/1998 | Jones et al. | |
| 6,130,355 A | 10/2000 | Jones | |
| 6,353,132 B1 | 3/2002 | Zoeller et al. | |
| 6,355,837 B1 | 3/2002 | Zoeller et al. | |
| 6,387,842 B1 | 5/2002 | Wegman et al. | |
| 6,521,783 B1 | 2/2003 | Wegman et al. | |
| 2003/0054951 A1 | 3/2003 | Zoeller et al. | |

FOREIGN PATENT DOCUMENTS

| | | |
|---|---|---|
| DE | 3606169 A1 | 8/1987 |
| EP | 0030110 A1 | 6/1981 |
| EP | 0453148 A1 | 10/1991 |
| EP | 0566370 A2 | 10/1993 |
| EP | 0566371 A2 | 10/1993 |
| EP | 0596632 A1 | 5/1994 |
| GB | 1185453 | 3/1970 |
| GB | 1277242 | 6/1972 |
| WO | WO 05/085162 A1 | 9/2005 |
| WO | WO 05/105720 A1 | 11/2005 |

OTHER PUBLICATIONS

Bagno, Alessandro et al.; "Superacid-Catalyzed Carbonylation of Methane, Methyl Halides, Methyl Alcohol, and Dimethyl Ether to Methyl Acetate and Acetic Acid"; 1990 *J. Org. Chem.*, vol. 55, pp. 4284-4289.
Ellis, Brian et al.; "Heterogeneous Catalysts for the Direct, Halide-free Carbonylation of Methanol"; 1996, *11th International Congress on Catalysis*, pp. 771-779.
Fujimoto, Kaoru et al.; "Vapor Phase Carbonylation of Methanol with Solid Acid Catalysts"; 1984, *Chemistry Letters*, pp. 2047-2050.
Sardesai, Abhay et al.; "Synthesis of Methyl Acetate from Dimethyl Ether Using Group VIII Metal Salts of Phosphotungstic Acid"; 2002, *Energy Sources*, vol. 24, pp. 301-317.
Volkova, G.G. et al.; "Heterogeneous catalysts for halide-free carbonylation of dimethyl ether"; 2002, *Catalysis Letters*, vol. 80, No. 3-4, pp. 175-179.
Volkova, G.G. et al.; "Solid superacids for halide-free carbonylation of dimethyl ether to methyl acetate"; 2004, *Elsevier B.V.*, 6 pages.
Wegman, Richard W.; "Vapour Phase Carbonylation of Methanol or Dimethyl Ether with Metal-ion Exchanged Heteropoly Acid Catalysts"; 1994, *J. Chem. Soc., Chem. Commun.*, pp. 947-948.
Ferrierite—http://www.britannica.com/eb/article?tocId=9034104, 1 page.
Barri, S.A.I. et al.; "Structure of Theta-1, the first unidimensional medium-pore high silica zeolite"; 1984, *Nature*, vol. 312, pp. 533-534.
Borade, Rmesh B. et al.; Synthesis of an iron silicate with the ferrierite structure; 1996, *Chem. Commun.*, pp. 2267-2268.
Bhat, S.D. et al.; "High temperature hydrothermal crystallization, morphology and yield control of zeolite type K-LTL"; 2004, *Microporous and Mesoporous Materials*, vol. 76, pp. 81-89.
Foster, M.D. et al.; "A geometric solution to the largest-free-sphere problem in zeolite frameworks"; 2006, *Microporous and Mesoporous Materials*, vol. 90, pp. 32-38.
Howden, M.G.; "Synthesis of offretite: Part 1, Using various organic compounds as templates"; 1987, *Zeolites*, vol. 7, pp. 255-259.
Jacob, N.E. et al.; "Crystallization of gallium analog of zeolite Nu-23/ferrierite"; 1993, *Zeolites*, vol. 13, pp. 430-434.
Martucci, Annalisa et al.; "Crystal structure of zeolite omega, the synthetic counterpart of the natural zeolite mazzite"; 2003, *Microporous and Mesoporous Materials*, vol. 63, pp. 33-42.

(Continued)

*Primary Examiner*—Paul A. Zucker
(74) *Attorney, Agent, or Firm*—Townsend and Townsend and Crew LLP

(57) ABSTRACT

A product comprising a lower alkyl ester of a lower aliphatic carboxylic acid is produced by a process comprising reacting a lower alkyl ether with carbon monoxide in the presence of a catalyst comprising mordenite and/or ferrierite, optionally including an additional framework metal such as gallium, boron and/or iron, under substantially anhydrous conditions. More specifically, methyl acetate is selectively produced by reaction of dimethyl ether with carbon monoxide in the presence of a catalyst comprising mordenite or ferrierite, under substantially anhydrous conditions.

29 Claims, 6 Drawing Sheets

OTHER PUBLICATIONS

Melian-Cabrera et al.; "Innovations in the synthesis of Fe-(exchanges)-zeolites"; 2005, *Catalysis Today*, vol. 110, pp. 255-263.

Sulikowski, Bogdan et al.; "Synthesis of a Novel Gallosilicate with the Ferrierite Structure"; 1989, *J. Chem. Soc. Chem. Commun.*, pp. 1289-1290.

Vaughan, D.E.W. et al.; "Synthesis of ECR-18--a synthetic analog of paulingite"; 1999, *Microporous and Mesoporous Materials*, vol. 28, pp. 233-239.

Zones, Stacey I. et al.; "Studies on the ROle of Fluoride Ion vs Reaction Concentration in Zeolite Synthesis"; 2005, *J. Phys. Chem.*, vol. 109, pp. 652-661.

Ferrierite-Mg, http://www.mindat.org/min-6931.html, 3 pages, No Date Provided.

Ferrierite Mineral Data, http://webmineral.com/data/Ferrierite.shtml, 5 pages, No Date Provided.

The Mineral Mordenite, http://mineral.galleries.com/galleries.com/minerals/silicate/mordenit/mordenit.html, 2 pages, No Date Provided.

Mordenite, http://www.minweb.co.uk/zeolites/morddata.html, 2 pages, No Date Provided.

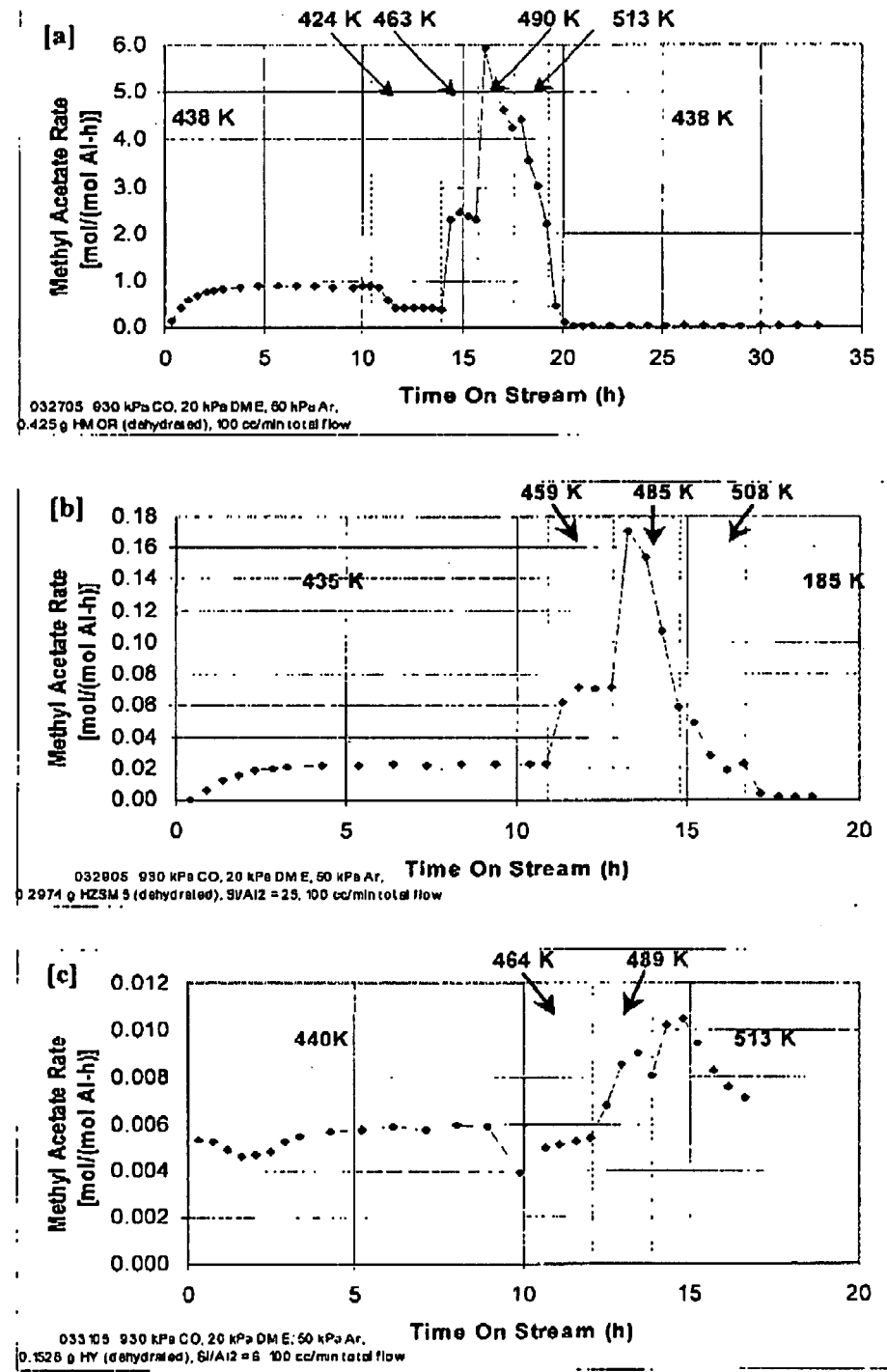
Figure 1. Methyl acetate formation rates on a) H-MOR (Si/Al = 10), b) H-ZSM5 (Si/Al = 12), c) H-Y (Si/Al = 3),

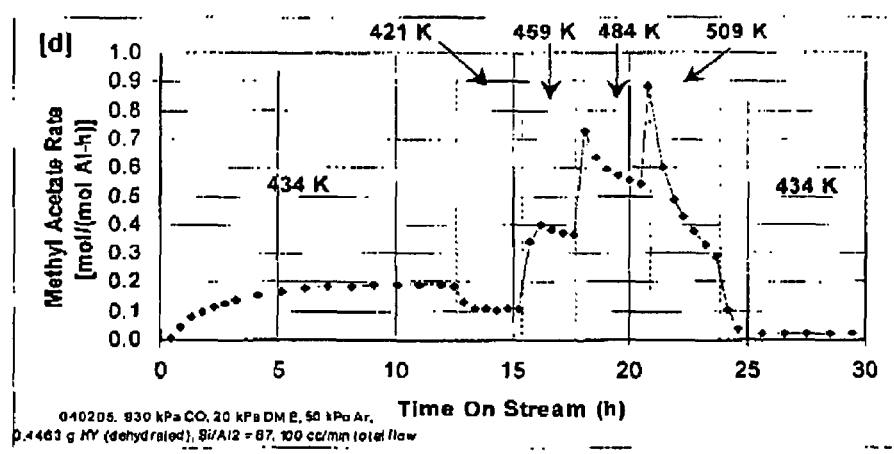
Figure 1 Continued. Methyl acetate formation rates on d) H-FER (Si/Al = 34) [930 kPa CO, 20 kPa DME, 50 kPa Ar].

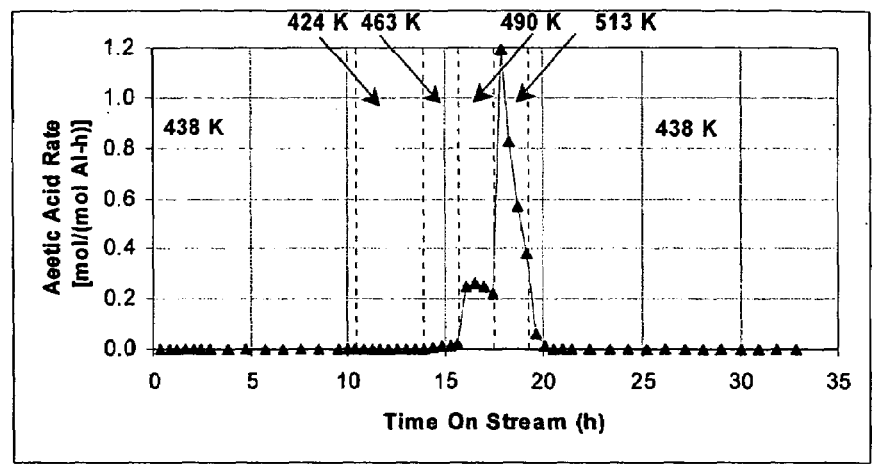
Figure 2. Acetic acid formation rates on H-MOR (Si/Al = 10) [930 kPa CO, 20 kPa DME, 50 kPa Ar].
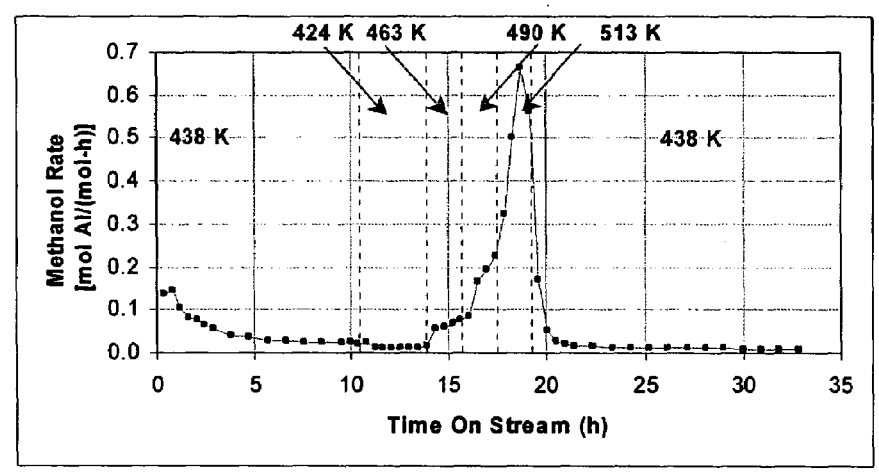
Figure 3. Methanol formation rates on H-MOR (Si/Al = 10) [930 kPa CO, 20 kPa DME, 50 kPa Ar].

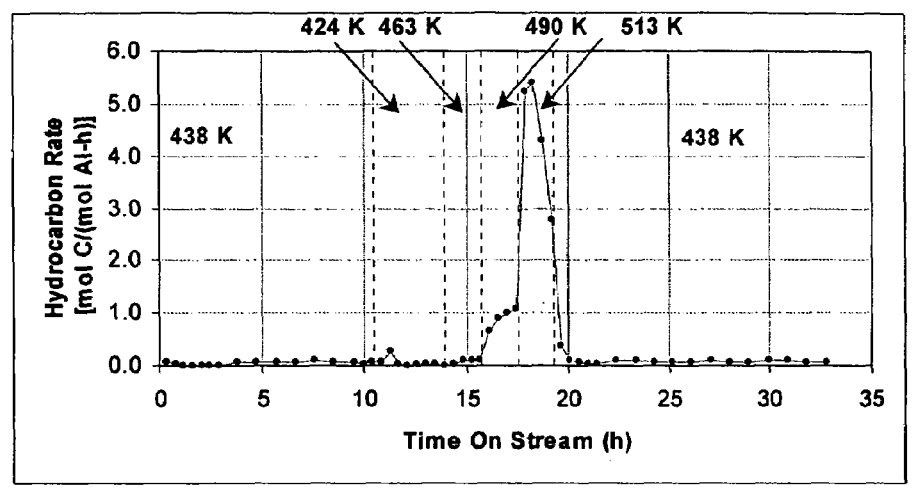
Figure 4. Hydrocarbon formation rates on H-MOR (Si/Al = 10) [930 kPa CO, 20 kPa DME, 50 kPa Ar].

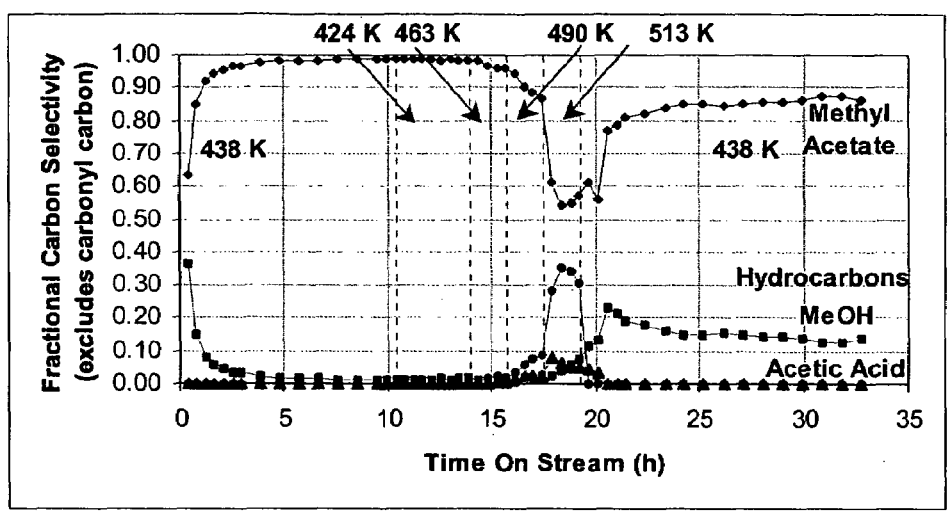
Figure 5. Product selectivities on H-MOR (Si/Al = 10) [930 kPa CO, 20 kPa DME, 50 kPa Ar].

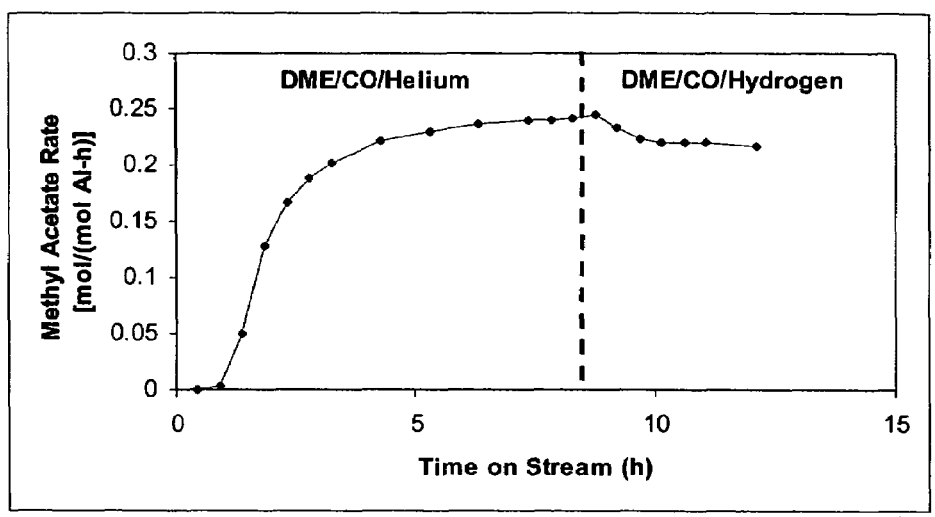
Figure 6. Methyl acetate rates on H-MOR (Si/Al = 10) [465 kPa CO, 20 kPa DME, 25 kPa Ar, 500 kPa helium or 500 kPa hydrogen, 438 K].

PROCESS FOR CARBONYLATION OF ALKYL ETHERS

This application is a continuation-in-part of application Ser. No. 11/123,581 filed May 5, 2005 now abandoned, the contents of all of which are incorporated herein by reference.

BACKGROUND OF THE INVENTION

This invention relates to an improved process for the production of methyl acetate from dimethyl ether, and more generally to the production of alkyl esters of aliphatic carboxylic acids, by the carbonylation of alkyl ethers. In another aspect this invention relates to the production of lower aliphatic carboxylic acids by first producing an alkyl ester from a lower alkyl ether, followed by hydrolysis of the ester to the acid. An example of this is the production of acetic acid by carbonylation of dimethyl ether, to form methyl acetate, followed by hydrolysis of the ester to produce acetic acid.

The most widely used industrial process for production of acetic acid is the carbonylation of methanol, which is described generally in British patents 1,185,453 and 1,277,242 and U.S. Pat. No. 3,689,533, for instance. In that type of process, methanol is reacted with carbon monoxide or a carbon monoxide-containing gas in the presence of a rhodium- or iridium-containing catalyst, in the additional presence of a halogen (usually iodine)-containing promoter. Though widely used, nonetheless these processes require the use of expensive corrosion-resistant alloys due to the presence of iodide and result in production of low levels of iodine-containing byproducts that are difficult to remove from the acetic acid by conventional distillation. Some non-halide based catalyst systems have been investigated for this reaction, but none have been commercialized, primarily due to issues with catalyst lifetime and selectivity.

Methyl acetate is an important compound used industrially in petrochemical processes, particularly as a feed for the production of acetic anhydride and/or acetic acid. Methyl acetate can also be used for the production of ethylidene diacetate, a precursor to vinyl acetate and polyvinyl acetate. Dimethyl ether may be readily produced from synthesis gas, and the cost of its production can be lower than that of methanol.

A number of patents describe processes in which methanol or a mixture of methanol and dimethyl ether is carbonylated in the presence of a catalyst. Typically the products are a mixture of acetic acid and methyl acetate, sometimes also including acetic anhydride. In those patents it is disclosed that one of the reactions that may occur is the carbonylation of dimethyl ether to form methyl acetate. Typically, however, dimethyl ether is not used as the sole or even as the primary component of the feed, but as a minor component in methanol streams.

For example, German OLS 3,606,169 of BASF AG discloses carbonylation of a mixture of methanol, methyl acetate and/or dimethyl ether to produce a product containing acetic acid, methyl acetate and/or dimethyl ether in the presence of a cobalt-containing zeolite catalyst. The preferred zeolites are those of the 10-ring pentasil type with pore sizes intermediate between those of 8-ring zeolite A and those of 12-ring zeolites X and Y.

Jones et al., U.S. Pat. No. 6,130,355, disclose a process for carbonylation of methanol and/or dimethyl ether to produce acetic acid using a catalyst composed of at least one Group VIII noble metal, a halogenated compound as cocatalyst, and an iodide salt as catalyst stabilizer. Other patents disclosing processes for production of acetic acid and/or methyl acetate, in which dimethyl ether may be present in the feed in a mixture with methanol include U.S. Pat. Nos. 6,353,132 and 6,355,837 and U.S. published application 2003/005495.1, all of Zoeller et al. U.S. Pat. Nos. 5,189,203, 5,286,900 (both of Hansen et al.) and 5,728,871 (Joensen et al.) disclose processes in which syngas is first used to produce methanol, which is then combined with dimethyl ether, and the mixture carbonylated to produce acetic acid as a major product.

Several other references investigated carbonylation of dimethyl ether as the primary or sole component of a feed using various catalysts. For example, Jones et al. (U.S. Pat. No. 5,763,654) disclose such a process in which the catalyst is a Group VIII noble metal catalyst, with a halide-containing cocatalyst and methyl iodide as a promoter. Water was present in the reactor, though according to the disclosure of this patent it was used at lower concentrations than typical in the prior art. The major product was acetic acid.

Wegman (U.S. Pat. No. 5,218,140) experimented primarily with the carbonylation of methanol to produce acetic acid using heteropolyacid catalysts. The patent contains a group of experiments in which the feed was dimethyl ether (Examples 28-33); however, in those experiments the conversion to methyl acetate was relatively low.

Sardesai et al. (*Energy Sources* 2002, 24:301) also carried out carbonylation of dimethyl ether with a number of heteropoly acid catalysts, which gave results that varied widely in terms of conversion and selectivity to methyl acetate. Bagno et al. (*J. Org. Chem.* 1990, 55:4284) ran such a reaction with so-called "super-acid" catalysts including $BF_3$ and triflic acid, again with varying results as to selectively to methyl acetate.

BRIEF SUMMARY OF THE INVENTION

In brief, this invention comprises a process for producing a product comprising a lower alkyl ester of a lower aliphatic carboxylic acid comprising reacting a lower alkyl ether with carbon monoxide in the presence of a catalyst comprising mordenite and/or ferrierite under substantially anhydrous conditions.

More specifically, the invention herein comprises a process for producing methyl acetate by reaction of dimethyl ether with carbon monoxide in the presence of a catalyst comprising mordenite and/or ferrierite, under substantially anhydrous conditions.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 depicts formation rates of methyl acetate using various zeolites as catalyst candidates for the process of this invention.

FIG. 2 depicts the formation rate of acetic acid using an H-mordenite zeolite catalyst for the process of this invention.

FIG. 3 depicts the formation rate of methanol using an H-mordenite zeolite catalyst for the process of this invention.

FIG. 4 depicts the formation rate of hydrocarbons using an H-mordenite zeolite catalyst for the process of this invention.

FIG. 5 depicts calculated product selectivities.

FIG. 6 depicts the formation rate of methyl acetate using H-mordenite zeolite catalyst in the presence (and absence) of hydrogen in the reactant mixture.

DETAILED DESCRIPTION OF THE INVENTION

In brief, this invention comprises a process for producing a product comprising a lower alkyl ester of a lower aliphatic carboxylic acid comprising reacting a lower alkyl ether with carbon monoxide in the presence of a catalyst comprising mordenite or ferrierite, under substantially anhydrous conditions.

More specifically, the invention herein comprises a process for producing methyl acetate by reaction of dimethyl ether with carbon monoxide in the presence of a catalyst comprising mordenite or ferrierite, under substantially anhydrous conditions.

One component of the feed to the process comprises (primarily) a lower alkyl ether, that is, a compound having the formula

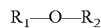

in which $R_1$ and $R_2$ are independently $C_1$-$C_6$ alkyl groups or $R_1$+$R_2$ together form a $C_2$-$C_6$ alkylene group. The total number of carbon atoms in groups $R_1$ and $R_2$, if $R_1$ and $R_2$ are alkyl groups, is from 2 to 12, preferably from 2 to 8, most preferably from 2 to 6. Preferably, $R_1$ and $R_2$ are straight-chain alkyl groups, most preferably straight-chain alkyl groups having from 1 to 3 carbon atoms each. If $R_1$+$R_2$ form an alkylene group (i.e., the ether is a cyclic ether), the total number of carbon atoms is preferably from 2 to 4.

The reaction overall can be depicted as

The term "alkyl" as used herein means a straight or branched chain, or cyclic, saturated aliphatic group, or a combination thereof, that has the number of carbon atoms designated (i.e. $C_3$ means three carbon atoms). Examples of acyclic alkyl groups include groups such as methyl, ethyl, n-propyl, isopropyl, n-butyl, t-butyl, isobutyl, sec-butyl, and the various pentyl and hexyl isomers. Examples of cyclical alkyl groups include cyclopropyl, cyclobutyl, cyclopentyl, and cyclohexyl. Combinations of cyclical and acyclic alkyl groups include, for example, cyclopropylmethyl, cyclobutylmethyl, cyclopropylethyl, etc.

The term "alkylene" as used herein refers to saturated aliphatic moieties that may form two single bonds with other moieties. This group includes, for example, methylene (—$CH_2$—), ethylene (—$CH_2CH_2$—) and hexylene [(—$CH_2$—)$_6$]. While alkylene groups may be straight or branched chain groups, straight-chain alkylene groups are preferred for use in the processes of this invention.

If the ether is a symmetrical ether, e.g. dimethyl ether, the main product will be the corresponding alkyl ester of an aliphatic acid (in this case, methyl acetate). If the ether is asymmetrical, the product will comprise one or both of the two possible carboxylic acid esters, depending on which of the two C—O bonds is cleaved in the reaction. For example, if the feed is methyl ethyl ether ($R_1$=methyl; $R_2$=ethyl), then the product will comprise ethyl acetate and/or methyl propionate.

A second component of the process is a feed comprising carbon monoxide. The feed may comprise substantially pure carbon monoxide (CO), for example, carbon monoxide typically provided by suppliers of industrial gases, or the feed may contain impurities that do not interfere with the conversion of the alkyl ether to the desired ester, such as hydrogen, nitrogen, helium, argon, methane and/or carbon dioxide. For example, the feed may comprise CO that is typically made commercially by removing hydrogen from synthesis gas via a cryogenic separation and/or use of a membrane.

The carbon monoxide feed may contain substantial amounts of hydrogen. For example, the feed may be what is commonly known as synthesis gas, i.e. any of a number of gaseous mixtures that are used for synthesizing a variety of organic or inorganic compounds, and particularly for ammonia synthesis. Synthesis gas typically results from reacting carbon-rich substances with steam (in a process known as steam reforming) or with steam and oxygen (a partial oxidation process). These gases contain mainly carbon monoxide and hydrogen, and may also contain smaller quantities of carbon dioxide and nitrogen. The ability to use synthesis gas provides another advantage over processes for producing acetic acid from methanol, namely the option of using a less expensive carbon monoxide feed. In methanol-to-acetic acid processes, the inclusion of hydrogen in the feed can result in production of unwanted hydrogenation byproducts; accordingly the feed should be high-purity carbon monoxide.

The catalyst is composed of mordenite or ferrierite, or mixtures or combinations of the two, either per se (i.e., in the acid form, generally referred to as H-mordenite and H-ferrierite), or optionally ion-exchanged or loaded with one or more metals such as copper, nickel, iridium, rhodium, platinum, palladium, or cobalt. Mordenite catalysts may, in addition to silicon and aluminum atoms, contain further elements in the zeolite framework, particularly gallium and/or iron. Ferrierite catalysts may, in addition to silicon and aluminum atoms, contain further elements in the zeolite framework, particularly boron, gallium and/or iron. Framework modifier elements to both types of catalysts may be introduced to the framework by any conventional means. Where a framework modifier element is used in either a mordenite or ferrierite catalyst, the catalyst suitably has a ratio of silica to the oxide of the framework modifier element would be from about 10:1 to about 100:1. T-atom incorporation where T is B, Ga or Fe into zeolites of the ferrierite structure is disclosed in Melian-Cabrera et al., *Catalysis Today* 110 (2005) 255-263; Shawki et al., EP (Application) 234,766 (1987), Sulikowski et al., *J. Chem. Soc., Chem. Comm.*, 1289 (1989); Borade et al., *J. Chem. Soc., Chem-.Comm.*, 2267 (1996); Jacob et al., *Zeolites* 430 (1993) Vol. 13. T-atom incorporation into zeolites of the mordenite structure where the T-atom is Ga or Fe is disclosed in Smith, WO 05/085162.

Mordenite (commonly available as Na-mordenite, $NH_4$-mordenite or H-mordenite) is a member of the aluminosilicate zeolite class of minerals. The formula of mordenite in its Na-form is usually given as $Na(AlSi_5O_{12}).3H_2O$ or $(Na_2,Ca,K_2)Al_2Si_{10}O_{24}.7H_2O$. It is available from a number of commercial sources of such materials. Ferrierite is another member of the aluminosilicate zeolite class of minerals, also available in the Na—, $NH_4$— and H-forms. In the Na-form its formula generally is given as $Na_{0.8}K_{0.2}MgSi_{15}Al_3O_{36}.9H_2O$ or $(Mg,Na_2,K_2,Ca)_{3-5}Mg[Al_{5-7}Si_{27.5-31}O_{72}].18H_2O$. It, too, is available from various commercial sources. Additional information on these materials can be found on the website of the International Zeolite Association, www.iza-online.org.

Because the reaction is to be conducted substantially in the absence of water, the catalyst should be dried before beginning the operation, for example, by preheating to 400-500° C.

In general, the process is run at temperatures at or below about 250° C., that is, at temperatures of from about 100 to about 250° C., preferably from about 150 to about 180° C. One feature of the process is that, surprisingly, the carbonylation of dimethyl ether (DME) to methyl acetate using mordenite zeolite based catalysts and in the substantial absence of water can be performed with very high selectivities at temperatures significantly lower than those cited in the prior art for methanol carbonylation. Additionally, under these conditions the mordenite is essentially inactive for the carbonylation of methanol. Reaction temperatures are kept within the above range also to minimize the dehydration of any methanol that may be present to form hydrocarbons and water, because the presence of water strongly inhibits the carbonylation of dimethyl ether to methyl acetate.

Typical operating pressures are from about 1 bar to about 100 bar, preferably with carbon monoxide pressures greater than 10 bar and dimethyl ether pressures below 5 bar.

The process is run under substantially anhydrous conditions, i.e. in the substantial absence of water. Water has been found to inhibit the carbonylation of dimethyl ether to form methyl acetate. This is in comparison to prior art processes in which dimethyl ether was a co-feed, and in which water was also fed to the reaction. Water is thus kept as low as feasible, in order to allow the desired reaction to proceed best. To accomplish this, the ether and carbon monoxide reactants and the catalyst are preferably dried prior to introduction into the process.

The process may be run as either a continuous or a batch process, with continuous processes typically preferred. Essentially, the process is a gas-phase operation, with reactants being introduced in either liquid or gaseous phase and products withdrawn as gases. As desired, the reaction products may subsequently be cooled and condensed. The catalyst may be used as convenient, in either a fixed bed or a fluidized bed. In operating the process, unreacted starting materials may be recovered and recycled to the reactor. The product methyl acetate may be recovered and sold as such, or may be forwarded to other chemical process units as desired. If desired, the entire reaction product may be sent to a chemical process unit for conversion of the methyl acetate and optionally other components to other useful products.

In one preferred embodiment of the invention the methyl acetate is recovered from the reaction products and contacted with water to form acetic acid via hydrolysis reactions. Alternatively, the entire product may be passed to a hydrolysis step, and acetic acid separated thereafter. The hydrolysis step may be carried out in the presence of an acid catalyst, and may take the form of a reactive distillation process, well known in the art.

After separation, alcohols produced in the hydrolysis reactor may be sent to a dehydration reactor to produce an ether, which can be separated from water and recycled to the carbonylation unit as fresh feed for the carbonylation reactor.

In another embodiment, the hydrolysis of the ester product to alcohol and carboxylic acid is performed by injecting water at one or more points in the catalyst bed, once a significant amount of ester has been produced by carbonylation. Injection of water in this manner essentially stops the conversion of dimethyl ether to methyl acetate, and removes the requirement for a separate hydrolysis reactor. The mordenite or ferrierite catalyst thus may also function as the acid catalyst for the hydrolysis of the ester product to give a carboxylic acid. If the reactor is a fluidized bed reactor, with back-mixing, then the reactor and catalyst will then have to be thoroughly dried before they are again used for the main process. If, on the other hand, the reactor is a tubular reactor, with staged introduction of water downstream of the main reaction zone, such drying should not be necessary.

Using a mordenite catalyst, conversions can be up to 100%, preferably from about 10% to about 100%, depending on the space velocity and reactant pressures used. Selectivity to methyl acetate has been shown to be constant, at values greater than 99% at 165° C. for over 10 hours. At 190° C., selectivities to methyl acetate are initially 96%, but decrease with time on stream. Such results are unexpected with the use of mordenite, and maintenance of a substantially anhydrous environment, as the prior art indicates that mordenite typically must be used for the conversion of methanol to acetic acid at temperatures substantially higher than 250° C. Such temperatures also can lead to deactivation of methanol carbonylation due to the formation of hydrocarbons, which can block catalyst pores and/or active sites. In addition, as will be seen in the Examples, experiments with other zeolites under similar conditions do not show the desired conversion and/or selectivity as mordenite and ferrierite.

Furthermore, as compared to prior art processes, there is relatively little product gasoline and/or other higher hydrocarbons. Often when methanol is used as a feed, there is a so-called "MTG" (methanol-to-gasoline) reaction that produces an undesirable high level of such hydrocarbons. Formation of methanol can occur in the early stages of the reaction; however, this can be minimized by pretreating the catalyst bed with dimethyl ether at typical reaction temperatures.

The following examples are presented as illustrative of the invention. However, they are not meant to limit the scope of this invention.

General Procedures

1) Catalyst Preparation

Catalysts were obtained commercially in the ammonium or acid form and pretreated in flowing dry air at 773 K for 3 hours.

| Catalyst | Source | Si/Al |
|---|---|---|
| H-MOR (mordenite) | Zeolyst International | 10 |
| H-MOR (mordenite) | Zeolyst International | 45 |
| H-FER (ferrierite) | Zeolyst International | 34 |
| H-ZSM5 | Al—Si Penta Zeolithe GmbH | 12.5 |
| H-Y | Engelhard Corporation | 3 |
| amorphous $SiO_2$—$Al_2O_3$ | Sigma-Aldrich | 6 |

2) Dimethyl Ether Carbonylation Reaction

Dimethyl ether carbonylation reactions were carried out in a fixed-bed stainless steel microreactor using 0.15-0.5 g catalyst. Catalysts were activated at 773 K in flowing dry air for 2 hours, cooled to reaction temperatures (150-240° C.), flushed with flowing dry helium, and pressurized to 10 bar before introducing reactants. The reactant mixture consisted of 20 kPa dimethyl ether, 930 kPa carbon monoxide, and 50 kPa argon, the latter as an internal standard (1 bar=101 kPa). All pretreatment and reactant streams were dried by passing through a calcium hydride bed (0.5 g, Aldrich) placed immediately before the reactor. Heat-traced lines (200-250° C.) were used to transfer the reactants and products to an on-line gas chromatograph (Agilent 6890) equipped with flame ionization and thermal conductivity detectors with methyl siloxane and Porapak® Q columns, respectively.

3) Dimethyl Ether Carbonylation Reaction with Synthesis Gas

Hydrogen addition experiments were carried out in the flow reactor described above. The reactant mixture consisted of 10 kPa dimethyl ether, 465 kPa carbon monoxide, 25 kPa argon, and 500 kPa helium or hydrogen. Helium, an unreactive diluent, was replaced by hydrogen after the catalyst system reached steady-state.

Experiments were conducted using the above-described procedure for carbonylation of dimethyl ether over seven catalysts in the temperature range of 148-335° C., with most experiments being conducted at 150-240° C., and 9.3 bar carbon monoxide. Catalysts included mordenite (H-MOR; Si/Al=10 and Si/Al=45), zeolite MFI (H-ZSM5; Si/Al=12), Y faujasite (H-Y; Si/Al=3) ferrierite (H-FER; Si/Al=34), and amorphous silica-alumina (Si/Al=6). Experimental conditions were: 10 bar total pressure, total flow=100 cm$^3$ (STP)/min, 2% DME/5% Ar/93% CO feed (passed over 0.5 g CaH$_2$ pre-reactor drying bed at ambient temperature) while increasing the temperature in steps between 144 and 335° C.

These experiments demonstrate that mordenite and ferrierite are far superior to other zeolite candidates for dimethyl ether carbonylation. Methyl acetate formation rates are shown in FIG. 1. Under the reaction conditions, rates at ~165° C. (normalized per Al) on H-MOR were nearly 50 times greater than those on H-ZSM5 and more than 150 times greater than those on H-Y. No deactivation was observed on any of the three zeolites at temperatures between 150 and 190° C. At higher temperatures (≧488 K), methyl acetate rates decreased with time on-stream, apparently as a result of the significant formation of large unreactive residues. This, if sufficiently extensive, can prevent the catalysts from returning to their initial carbonylation rates when tested again at lower temperatures (165-185° C.).

On H-Y at temperatures ≧488 K, the reactor effluent contained a broad range of hydrocarbons including several that overlapped with methyl acetate and methanol in the gas chromatogram. Therefore, at these temperatures, the reported methyl acetate and methanol formation rates on H-Y may be somewhat larger than their true formation rates.

FIGS. 2 and 3 show acetic acid and methanol formation rates on H-MOR. Acetic acid forms via methyl acetate hydrolysis or methanol carbonylation at temperatures ≧490 K on H-MOR. Methanol cannot form from dimethyl ether in the absence of water, which may be formed, however, as a by-product of MTG (methane-to-gasoline) reactions. The initial methanol formation rates reflect reactions of either residual water or of water formed from hydroxyl groups remaining in zeolites after catalyst pre-treatment (drying) at 500° C. Therefore, when detectable steady-state methanol rates are observed above 463 K, hydrocarbons are presumably being formed, even if they are not detected in the effluent by gas chromatography. Hydrocarbon formation rates (calculated as the dimethyl ether converted to products other than methyl acetate, acetic acid, or methanol) on H-MOR are shown in FIG. 4. No acetic acid was observed on the other zeolites. Product selectivities are shown in FIG. 5.

Low-aluminum content H-MOR (Si/Al=45) and amorphous silica alumina (Si/Al=6) were also tested over a broad range of temperatures (160-335° C.).

Carbonylation rates (per Al) on low aluminum content H-MOR were an order of magnitude smaller than those reported for the higher aluminum content H-MOR (Si/Al=10). The lower carbonylation activity (per Al) is not completely unexpected for this material because it shows higher hydrocarbon formation rates. Methanol (and DME)-to-hydrocarbon reactions form water in stoichiometric amounts; our studies have shown the requirement of anhydrous conditions for carbonylation activity. A dry environment is not possible in the presence of concurrent reactions that form hydrocarbons.

Amorphous silica-alumina (surface area=440 m$^2$/g) also was tested, for comparison. It began to show slight carbonylation activity at 259° C. Carbonylation rates on this material are 3-4 orders of magnitude lower than on H-MOR (Si/Al=10) at this temperature.

A summary of the above-described tests is presented below in Table 1.

TABLE 1

Steady-state product formation rates and acetyl carbon selectivity.

| | T(K) | Acetyl Rate [mol/(mol Al-h)] | MeOH Rate [mol/(mol Al-h)] | Hydrocarbon Rate [mol C/(mol Al-h)] | Acetyl Carbon Selectivity (%)** |
|---|---|---|---|---|---|
| H-MOR | | | | | |
| Si/Al = 10 | 424 | 0.4 | 0.011 | 0 | 99 |
| 0.425 g | 438 | 0.9 | 0.023 | 0 | 99 |
| | 463 | 2.7 | 0.055 | 0.02 | 96 |
| | 490 | 7.1* | | | |
| | 513 | deactivates | | | |
| H-FER | | | | | |
| Si/Al = 34 | 421 | 0.11 | 0 | 0 | 100 |
| 0.446 g | 434 | 0.19 | 0.012 | 0 | 97 |
| | 459 | 0.40 | 0.045 | 0 | 94 |
| | 484 | 0.73* | | | |
| | 509 | deactivates | | | |
| H-ZSM5 | | | | | |
| Si/Al = 6 | 435 | 0.023 | 0.116 | 0.22 | 12 |
| 0.297 g | 459 | 0.072 | 0.338 | 0.52 | 14 |
| | 485 | 0.171* | | | |
| | 508 | deactivates | | | |

TABLE 1-continued

Steady-state product formation rates and acetyl carbon selectivity.

| | T(K) | Acetyl Rate [mol/(mol Al-h)] | MeOH Rate [mol/(mol Al-h)] | Hydrocarbon Rate [mol C/(mol Al-h)] | Acetyl Carbon Selectivity (%)** |
|---|---|---|---|---|---|
| H-Y | | | | | |
| Si/Al = 3 | 440 | <0.01 | 0.14 | 0.22 | 3 |
| 0.153 g | 464 | <0.01 | 0.38 | 0.86 | <1 |
| | 489 | <0.01 | | | |
| | 513 | ~0.01 | | | |
| H-MOR | | | | | |
| Si/Al = 45 | 433 | 0.065 | 0.096 | 0.22 | 29 |
| .427 g | 451 | 0.125 | 0.27 | 0.3 | 30 |
| | 471 | 0.233 | 0.68 | 0.96 | 22 |
| | 492 | 0.425 | 1.52 | 3.9 | 14 |
| | 506 | 0.696 | 2.49 | 5.3 | 15 |
| Amorphous Silica Alumina | | | | | |
| Si/Al = 6 | 438 | 0 | 0 | 0 | 0 |
| .5476 g | 485 | 0 | 0 | 0 | 0 |
| | 532 | 0.004 | 0.012 | 0.05 | 11 |
| | 582 | 0.05 | 0.23 | 0.15 | 21 |
| | 608 | 0.1 | 0.4 | 0.18 | 26 |

*Acetyl formation rates after 25 minutes at corresponding temperature, catalyst deactivates.
**Acetyl carbon selectivity does not include carbonyl carbon Studies with Synthesis Gas H-Mordenite was evaluated for dimethyl ether carbonylation in the presence of hydrogen. Carbonylation rates are essentially unaffected by the presence of hydrogen as one-half of the total reactant feedstock (FIG. 6). Synthesis gas of various hydrogen:carbon monoxide ratios can be utilized without affecting dimethyl ether carbonylation rates.

Incorporation of Framework Metals

GaAl/Si)$NH_4$-mordenite ($SiO_2/Ga_2O_3$~39.2 and $SiO_2/Al_2O_3$~19.4) was converted from the ammonium form and tested for DME carbonylation under the following conditions. The sample was treated in flowing dry air (3.33 cm3s−1) at 773 K (0.0167 K s−1) for 3 h to convert it from the NH4+ form to the H+ form. DME carbonylation rates were measured in a packed-bed stainless steel reactor (8.1 mm ID, 9.5 mm OD) held within a three-zone resistively heated furnace. The catalyst sample (0.5 g, 185-250 mm particle diameter) was treated in flowing dry air (~1.67 cm3 s−1 g−1, zero grade, Praxair) for 3 h at 773 K (0.0167 K s−1) before cooling in flowing He (~3.33 cm3 s−1 g−1, UHP Praxair) to reaction temperature (438 K) and a mixture of 2% DME/5% Ar/93% CO (99.5% DME, Praxair; UHP Ar/CO, Praxair) was then fed.

The catalytic results were compared to H-mordenite (H-MOR) (supplier-Zeolyst) tested under the same conditions, Table 1.

TABLE 1

Comparison of (GaAl/Si)H-mordenite and (Al/Si)H-mordenite samples a

| | (GaAl/Si)H-mordenite | H-mordenite (Zeolyst, Si/Al = 10) |
|---|---|---|
| Rate [mols/g-atom Al/h] | 0.54 | 0.9 |
| Space Time Yield [g-MeOAc/g-zeolite/h] | 0.061 | 0.103 | a 930 kPa CO, 20 kPa DME, 50 kPa Ar, 438 K

Al—Si ratio

A series of runs was carried out using catalysts with various Al:Si ratios. Table 2 contains a list of H-MOR samples and corresponding rates [mol/g-atom Al/h] and space time yields [g MeOAc/kg zeolite/h]. Typically 0.5 g of sample was used at 438 K with total pressures of 10 Atm (20 kPa DME, 50 kPa Ar, 930 kPa CO) and a flow of 1.67 cm3/s. These showed some quite good rates in terms of mol kg$^{-1}$ h$^{-1}$. The results show that the productivity per mass of catalyst (and presumably volume) can be increased by changing the Si to Al ratio.

TABLE 2

DME Carbonylation Rates and Space Time Yields as a function of Al-content in H-MOR

| Sample | Rate [mol/g-atom Al/h] | Space time yield [g MeOAc/kg zeolite/h] |
|---|---|---|
| H-MOR (Zeolyst, Si/Al = 9.8) | 0.9 | 102.7 |
| H-MOR (Tosoh, BP Chemicals, Si/Al = 8.9) | 0.74 | 92.1 |
| H-MOR (Zeolyst, BP Chemicals, Si/Al = 9.5) | 0.94 | 110.4 |
| H-MOR (Sud-Chemie, BP Chemicals, Si/Al = 10.1) | 0.5 | 55.5 |
| H-MOR (Zeolyst, Si/Al = 6.5) | 0.99 | 162.8 |
| H-MOR (Zeolyst, Si/Al = 44.5) | 0.08 | 2.1 |

Conditions: 930 kPa CO, 20 kPa DME, 50 kPa Ar; 438 K; 3.33 cm$^3$g$^{-1}$s$^{-1}$.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A process for producing a product comprising a lower alkyl ester of a lower aliphatic carboxylic acid having the formula $R_1$—COO—$R_2$ comprising reacting a lower alkyl ether having the formula $R_1$—O—$R_2$ in which $R_1$ and $R_2$ are independently $C_1$-$C_6$ alkyl groups, providing that the total number of carbon atoms in groups $R_1$ and $R_2$ is from 2 to 12, or $R_1$ and $R_2$ together form a $C_2$-$C_6$ alkylene group, with a carbon monoxide-containing feed in the presence of a catalyst comprising mordenite and/or ferrierite, under substantially anhydrous conditions.

2. A process according to claim 1 in which the ester is methyl acetate and the ether is dimethyl ether.

3. A process according to claim 1 in which the catalyst is H-mordenite.

4. A process according to claim 1 in which the temperature is from about 100° C. to about 250° C.

5. A process according to claim 1 in which the temperature is from about 150° C. to about 180° C.

6. A process according to claim 1 in which the catalyst comprises a fixed bed of catalyst.

7. A process according to claim 1 in which the catalyst comprises a fluidized bed of catalyst.

8. A continuous process according to claim 1.

9. A batch process according to claim 1.

10. A process according to claim 1 in which the carbon monoxide-containing feed further comprises hydrogen.

11. A process according to claim 10 in which the carbon monoxide-containing feed comprises a synthesis gas.

12. A process according to claim 1 further comprising hydrolyzing the ester to produce the corresponding carboxylic acid.

13. A process according to claim 2 comprising further hydrolyzing the methyl acetate to produce acetic acid.

14. A process according to claim 12 or 13 in which the hydrolysis is conducted in a separate reactor from the ester-producing reaction.

15. A process according to claim 12 or 13 in which the hydrolysis is conducted in the same reactor as the ester-producing reaction.

16. A process according to claim 1 in which $R_1$ and $R_2$ are $C_1$-$C_6$ alkyl groups.

17. A process according to claim 1 in which $R_1$ and $R_2$ are straight chain $C_1$-$C_6$ alkyl groups.

18. A process according to claim 1 in which $R_1$ and $R_2$ are straight chain alkyl groups having from 1 to 3 carbons each.

19. A process according to claim 16 in which the alkyl groups contain a total of from 2 to 8 carbon atoms.

20. A process according to claim 19 in which the alkyl groups are straight-chain alkyl groups.

21. A process according to claim 16 in which the alkyl groups contain a total of from 2 to 6 carbon atoms.

22. A process according to claim 1 in which $R_1$ and $R_2$ together form a $C_2$-$C_6$ alkylene group.

23. A process according to claim 1 in which $R_1$ and $R_2$ together form a straight-chain $C_2$-$C_6$ alkylene group.

24. A process according to claim 1 in which $R_1$ and $R_2$ together form a $C_2$-$C_4$ alkylene group.

25. A process according to claim 1 in which the catalyst contains one or more additional framework metals.

26. A process according to claim 25 in which the framework metals are selected from gallium, boron and iron.

27. A process according to claim 25 in which the framework metal is gallium.

28. A process according to claim 25 in which the catalyst comprises mordenite and the framework metal is selected from gallium and/or boron.

29. A process according to claim 25 in which the catalyst comprises ferrierite and the framework metal is selected from gallium, boron and/or iron.

* * * * *